US008118427B2

(12) United States Patent
Bonnin et al.

(10) Patent No.: US 8,118,427 B2
(45) Date of Patent: Feb. 21, 2012

(54) METHOD FOR OPTIMIZING AND/OR MANUFACTURING EYEGLASS LENSES

(75) Inventors: Thierry Bonnin, Charenton-le-Pont (FR); Marie-Gaelle Froeliger, Charenton le Pont (FR); Martha Hernandez, Charenton le Pont (FR); Gildas Marin, Charenton le Pont (FR)

(73) Assignee: Essilor International (Compagnie General d'optique), Charenton le Pont (FR)

( * ) Notice: Subject to any disclaimer, the term of this patent is extended or adjusted under 35 U.S.C. 154(b) by 57 days.

(21) Appl. No.: 12/302,636

(22) PCT Filed: May 24, 2007

(86) PCT No.: PCT/IB2007/001364
§ 371 (c)(1),
(2), (4) Date: Apr. 22, 2009

(87) PCT Pub. No.: WO2007/138428
PCT Pub. Date: Dec. 6, 2007

(65) Prior Publication Data
US 2009/0219486 A1 Sep. 3, 2009

(30) Foreign Application Priority Data
May 29, 2006 (EP) .................................... 06290863

(51) Int. Cl.
*G02C 7/02* (2006.01)
*A61B 3/02* (2006.01)
*A61B 3/00* (2006.01)
(52) U.S. Cl. ......... 351/177; 351/246; 351/247; 351/237
(58) Field of Classification Search .................. 351/177, 351/246, 247
See application file for complete search history.

(56) References Cited

U.S. PATENT DOCUMENTS

| 5,311,356 | A | * | 5/1994 | Freilich | 359/467 |
| 6,160,666 | A | | 12/2000 | Rallison et al. | |
| 6,692,127 | B2 | * | 2/2004 | Abitbol et al. | 351/227 |
| 2002/0180931 | A1 | * | 12/2002 | Dick et al. | 351/211 |
| 2006/0087618 | A1 | * | 4/2006 | Smart et al. | 351/222 |
| 2006/0220953 | A1 | * | 10/2006 | Roddy et al. | 342/176 |

FOREIGN PATENT DOCUMENTS

EP 898930 3/1999

(Continued)

OTHER PUBLICATIONS

Legras et al., "A Method for Simulation of Foveal Vision During Wear of Corrective Lenses," *Optometry and Vision Science*, vol. 81, No. 9, pp. 729-738 (2004).

*Primary Examiner* — Ricky Mack
*Assistant Examiner* — Zachary Wilkes
(74) *Attorney, Agent, or Firm* — Occhiuti Rohlicek & Tsao LLP (57) ABSTRACT

A method for determining an optimal eyeglass lenses design for a viewer (1) comprising the successive steps of: showing the viewer (1) a stereoscopic scene including optical effects of a first lens design;—introducing a relative movement between the viewer (1) and the shown stereoscopic scene, said scene being shown with optical effects of the first lens design; expressing the viewer's opinion; showing the viewer (1) a stereoscopic scene including optical effects of a modified lens design; introducing a relative movement between the viewer (1) and the shown stereoscopic scene, said scene being shown with the modified lens optical effects; expressing again the viewer's opinion; repeating the three last steps up to viewer's satisfaction. A system for customizing vision correction suitable to implement said method. Related computer program for dynamically calculating a stereoscopic image. Related computer program for actuating an electro-active component.

22 Claims, 6 Drawing Sheets

FOREIGN PATENT DOCUMENTS

| | | |
|---|---|---|
| EP | 1468649 | 10/2004 |
| EP | 1018691 | 3/2005 |
| EP | 0734683 | 10/2005 |
| JP | 11-120213 | 4/1999 |
| JP | 2005261690 | 9/2005 |
| WO | 2005/050290 | 6/2005 |
| WO | WO2005050290 | 6/2005 |
| WO | 2005/107576 | 11/2005 |
| WO | 2007/056795 | 5/2007 |

* cited by examiner

METHOD FOR OPTIMIZING AND/OR MANUFACTURING EYEGLASS LENSES

CROSS-REFERENCE TO RELATED APPLICATIONS

This application is the National Stage of International Application No. PCT/IB2007/001364, filed on May 24, 2007, which claims the priority of European Application No. 06290863.7, filed on May 29, 2006. The contents of both applications are hereby incorporated by reference in their entirety.

BACKGROUND

The present invention relates to methods and systems for manufacturing eyeglass lenses.

SUMMARY

A method for customizing vision correction traditionally includes measuring optical aberration data of a patient's eye, usually performed by optometrists or ophthalmologists, determining the lens parameters and offering to the patient a plurality of model lenses with different lens "designs".

The patient's vision parameters are measured using for example trial lenses, an aberrometer, a wave-front sensor, grating or other known method and/or apparatus.

Other vision parameters can be obtained such as the patient's vertex distance, pupil size, pupil distance, frame information, gaze directions.

The optical surface, or "design" imparts the optical correction of the material. Given the infinite number of eyesight corrections, the numbers of designs is almost infinite.

For cost and manufacture reasons, only a limited number of "model designs" is predetermined by the lens manufacturers.

Such "model designs" are of great importance when considering progressive addition lenses (PAL).

PAL have gained worldwide acceptance as the most performant ophthalmic lenses for correction of presbyopia because they provide comfortable vision at all distances.

A PAL is designed not only to restore a presbyope's ability to see clearly at all distances but also to optimally respect all physiological visual functions, in particular:
  foveal vision where coordination of the body, head and eye movements, in relation to the objects' location in the vision, defines the power value needed at each point of the progression. The field of gaze is determined by the natural coordination of horizontal eye and head movements;
  extra-foveal vision (provided by the periphery of the retina) which provides space and form perception and is directly influenced by the distribution of prism on the progressive lens surface. The variation of prismatic effects plays also a role in the viewer's comfort when movement is perceived;
  binocular vision where, for optimal fusion of the simultaneous perception of the two eyes, the images produced by the right and left lenses must be formed on corresponding retinal points and display similar optical properties in all directions of gaze.

Progressive lens designers work towards respecting these physiological functions and propose a limited number of optimized designs which are tested through rigorous clinical trials. A plurality of "model designs" is offered by each lens maker.

The optometrist or ophthalmologist proposes a lens "model design" that may be the result of an analysis of the viewing behavior of the patient and a semi-finished lens with said "model design" is tooled, namely edged and polished, to obtain the final patient's lenses.

The semi-finished lens is a prefabricated lens where usually only a face is machined to fit the patient's vision parameters.

The viewer has an actual perception of his corrected vision only when wearing the manufactured lens.

Even though this customizing method is widely used, there is still a need for improved lenses customizing method.

This is mainly due to the fact that there is usually no exact relationship between lens design calculations and a particular viewer's satisfaction.

To improve customizing vision correction a method has been disclosed in patent publication WO 2005/05 0290, where said method comprises measuring optical aberration data of a patient's eye, calculating a lens definition based on the optical aberration data, wherein calculating the lens definition comprises calculating a correction of at least one low order aberration and at least one high order aberration, and fabricating a correcting lens based on said lens definition.

Such a method makes possible to enhance the number of possible lens design but does not take into account the real perception of the viewer and a low satisfaction level can result of it. Furthermore the mathematical assumptions are rather complicated and the calculating time may be long, and then limiting the number of successive trials.

Another attempt to customize vision correction has been developed and commercialized by ESSILOR INTERNATIONAL under the trademark Varilux Ipseo. A device is used to measure the head-eye movement ratio, which corresponds to a visual imprint of the particular viewer, and personalized progressive lenses are manufactured after processing the data to create a design which matches physiological characteristics of the viewer.

Such a method is useful to enhance the vision comfort of the viewer, but the actual vision perception of the corrected vision is still possible only after manufacturing corresponding lenses.

Accordingly there remains a need for improving the satisfaction level of a viewer when customizing his vision correction.

SUMMARY

Thus the goal of the present invention is to improve the method and apparatus for customizing eyeglass lenses, in particular PAL, and to minimize the gap between the lens viewer's expectations and the actual manufactured eyeglass lenses wearing perception for the viewer.

This object is obtained according to the invention by a method for determining an optimal eyeglass lenses design for a viewer comprising the successive steps of:
  showing the viewer a stereoscopic scene including optical effects of a first lens design;
  introducing a relative movement between the viewer and the shown stereoscopic scene, said scene being shown with optical effects of the first lens design;
  expressing the viewer's opinion;
  showing the viewer a stereoscopic scene including optical effects of a modified lens design;
  introducing a relative movement between the viewer and the shown stereoscopic scene, said scene being shown with the modified lens optical effects;
  expressing again the viewer's opinion;
  repeating the three last steps up to viewer's satisfaction.

It is then possible to take into account how things are seen, with fluctuation, deformation, blur and the like, while wearing a lens such as a PAL, in particular when the movement of turning the eye and/or the head occurs to view the scene.

Blur effects in the different head positions are taken into account. As the perception and the sensitiveness to such blur effects differs from a viewer to another, the viewer can choose the lens design which most enhance his vision comfort.

According to the present invention "optical effects" are the optical distortions due to a lens design.

The far vision parameters are not taken into account and the method is preferably used when the viewer is wearing lenses able to correct his far vision anomalies.

Wearing contact lens may be advantageous because such lenses follow the eye movements.

The viewer is thus able to "test" different lens designs and to choose the optimal design adapted for his vision behavior, without manufacturing the actual lenses. The optimal design parameters are then transmitted to a manufacturing device.

The process of the invention can also be used advantageously to elaborate new "model designs" with a low cost determination process where clinical trials are implemented using the process of the invention which is suitable to test a large number of vision parameters without manufacturing corresponding actual lenses.

According to a first embodiment of the present invention, the viewer's head position is determined and the stereoscopic scene is a stereoscopic projected image calculated as a result of the lens design and the viewer's head position This embodiment uses virtual reality simulation. Viewer's head position and movement is determined for example by a head movement tracker. The scene may be projected on a screen, for example a three screens stereoscopic display with 120° field of view, or on a hemispheric screen, or on a stereoscopic head mounted display (HMD). Electro-active shutter glass or polarized eye glass lenses, which are free of optical effect, may be used to obtain a stereoscopic vision with screen display configurations.

It is advantageous to avoid considering viewer's eye position. Only optical effects linked to central vision have then to be calculated.

According to an embodiment, the process further includes a calibration test. Calibration includes advantageously determination of the centre of rotation of the viewer's eyes when considering the position sensor reference frame. The viewer may adjust the position of edges of virtual lenses and compare them to actual calibration lenses.

Calibration may also include a calibration of the viewing system in order to respect the scale of the scene as a function of an initial position of the viewer.

According to an embodiment, the modification of the viewer's head position determination and the projection of calculated stereoscopic scene are dynamic.

In the frame of the present invention, "dynamic" has to be understood as a succession of scene corresponding to a frequency equal to or at least 10 Hz. Following a preferred embodiment, said frequency is 60 Hz for each eye, which corresponds to a video signal of 120 Hz. Said embodiment corresponds to the vision of a stereoscopic scene.

When introducing a dynamic behaviour, new selective situations are introduced, such as swim effect situation, magnification effect situation, astigmatism effect situation and other aberration effect situation.

The viewer can experience the actual visual feeling wearing virtually different lens designs when he and the scene are moving, in particular when accelerations occur.

Swim effects occur for example with PAL lens when movement is introduced.

Magnification effects are in particular encountered when moving when wearing unifocal lenses.

Astigmatism effects may occur when shaking or nodding one's head.

According to an embodiment, the stereoscopic scene is calculated by means of an operating unit comprising a lens design data base.

Lens design data base includes for example the surface characteristics and corresponding dioptric power of several model lens designs.

According to an embodiment, the stereoscopic scene is calculated by means of an operating unit comprising an optical effect data base.

Optical effect database includes for example precalculated optical effect linked to lens characteristics.

According to an embodiment, the optical effect data base is used to approximate the dynamically projected stereoscopic scene.

It is a major discovery of the invention to notice that the level of approximation to test a lens design is significantly lower when using a dynamic behaviour of the viewer compared to a static behavior, but resulting to the same level of visual perception quality. It is thus possible to calculate dynamically the stereoscopic scene with first order approximation and standard computers may be used to implement the method.

According to an embodiment, the approximation to calculate the stereoscopic scene is based on distortion estimation calculated in a given plan independently of the actual distance of the object of the scene, using for example ray tracing.

Optical effects, such as distortion and/or blur effects, are added to the final scene to be projected. Optical effects are calculated by ray tracing. They are for example firstly calculated on a limited number of points of a meshing, said points being situated in a medium plan of the scene and the calculation is performed when considering the initial viewer position. Optical effects are then added in real time and are interpolated taking advantage of pre-calculated data.

The meshing can be linear or quadratic.

According to another embodiment, the stereoscopic scene is an actual scene observed by the viewer through a device comprising an electro-active or opto-active component suitable to reproduce the optical effect of a given lens design.

Said active component is for example part of trial lenses. The active component can be pixellized and it is then possible to address specifically each zone with a chosen phase function corresponding to a lens design.

The viewer can then wear said trial lenses which design can be easily changed during the lenses selection process.

He thus has the opportunity to test a large number of lens design and to choose the optimum one.

The actual scene can be a real scene around the viewer or a projected scene.

According to an embodiment, the electro-active component is a deformable mirror.

According to an embodiment, the incident beam is firstly reflected on a plane mirror and directed to the deformable mirror on which it is reflected and directed to the viewer's eyes.

According to an embodiment, the incident beam is firstly polarised, then reflected on a semi-reflective mirror and directed to the deformable mirror, then directed through the semi-reflective mirror to a plan mirror and then directed to the viewer's eyes after being reflected on the semi-reflective mirror.

According to an embodiment, the deformable mirror is a piezoelectric deformable mirror.

The deformable mirror is for example a channel piezoelectric deformable mirror. It consists of piezoelectric column activators bonded to a base holder and where a reflective plate is bonded to the top of the activator structure and coated to form a mirror. The shape of the face plate is controlled by the voltages applied to the actuators.

Such channel piezoelectric deformable mirror are for example commercialized by the company Flexible Optical BV under the trade name "OKO Technologies".

19 Channel piezoelectric deformable mirror system of OKO Technologies has been successfully used in the frame of the present invention.

According to an embodiment, the electro-active or opto-active component is a spatial light modulator, which can be addressed electrically or optically respectively.

Spatial light modulators (SLM) imposes some form of spatially-varying modulation on a light beam. As it is possible to vary intensity, to modulate the phase and control polarity of the beam when addressing the pixels of the SLM, it is possible to modulate the image viewed by the viewer as it would have been modulated by a specific lens design.

Liquid crystals SLM have been advantageously used in the frame of the present invention. Said liquid crystals SLM can be optically (OA) or electrically (OE) addressed. OA SLM are mounted like mirrors, where OE SLM can be mounted in reflection or in transmission.

According to an embodiment, the spatial light modulator is an electrically addressed liquid crystals SLM and is mounted so that the incident beam be transmitted.

According to an embodiment, the initial lens design is determined using standard vision correction measurement of the viewer.

According to an embodiment, a number of vision parameters are selected and test sequences are performed parameter by parameter, the viewer's opinion being expressed during each sequence corresponding to each parameter.

According to an embodiment, the influence of a vision parameter choice is tested on previous determined vision parameters, and if the result is unsatisfactory, a new test sequence is performed with previous determined vision parameters up to viewer's satisfaction.

According to an embodiment, vision parameters are chosen from the list constituted of: progression length, near vision inset, eye/head coefficient, curvature of the lens.

According to an embodiment, the method further comprises the step of transmitting data corresponding to optimal lenses design to a manufacturing unit.

According to an embodiment, the manufacturing unit is a lens printer, such as an ultraviolet engraving system or a direct machining tool.

The invention also relates to a system for customizing vision correction of eyeglass lenses comprising means to show a stereoscopic scene including optical effects of a lens design to a viewer, said means being suitable to show the stereoscopic scene in different head positions of the viewer.

According to an embodiment, the system further comprises:
- a measurement system configured to determine viewer's head position;
- a calculation system configured to receive the measured head position and data of a lens design so as to calculate its optical effect and to apply a metric so as to calculate a stereoscopic scene corresponding to the image seen by the patient in the determined position;
- a projecting system of said calculated stereoscopic image to the viewer's eyes;

According to an embodiment, data of the lens design are optical distortion data.

According to an embodiment, data further comprises a set of parameters related to the given lens.

According to an embodiment, the measurement system comprises a head movement tracker.

According to an embodiment, head movement tracker is intended to be placed on the top of the head of the viewer.

According to an embodiment, the calculation system is fed by a lens design data base.

According to an embodiment, the calculation system is further configured to apply the metric using distortion approximation calculation in a given plan independently of the actual distance of the object of the scene.

According to an embodiment, the projecting system of the stereoscopic image includes a projector and a screen.

According to an embodiment, the screen is a three part screen with 120° field of view.

According to an embodiment, the projecting system of the stereoscopic images includes a stereoscopic head mounted display.

According to another embodiment, means to show a stereoscopic scene include an electro-active component suitable to reproduce the optical effect of a given lens design.

According to an embodiment, the electro-active component is a deformable mirror, for example a piezoelectric deformable mirror.

According to an embodiment, the electro-active component is a spatial light modulator.

According to still another embodiment, the system further comprises a selection system activated by the viewer to feed back his opinion.

According to an embodiment, the system is further configured to choose a new set of parameters of a lens as a function of the response of the selection system when activated by the patient's feedback.

According to an embodiment, the system further comprises a fabrication system configured to produce correcting eyeglass lenses based on lenses parameters including the result of the feedback of the viewer.

According to an embodiment, the fabrication system includes a lens printer, such as an ultraviolet engraving system or a direct machining tool.

The invention relates also to a computer program for dynamically calculating a stereoscopic scene where input parameters are:
- viewer's head position parameters
- viewer's satisfaction parameters
- lens design data base.

The invention relates also to a computer program for actuating an electro-active component where input parameters comprise:
- viewer's satisfaction parameters
- lens design data base.

The invention is further described in the detailed description of non-limiting embodiments as depicted and explained below.

BRIEF DESCRIPTION OF THE DRAWINGS

FIG. 4 shows a diagrammatic view (side view: FIG. 4a, frontal view: FIG. 4b) of a system according to the invention to implement the process of the invention where a device including an electro-active component is used;

FIG. 6 shows a diagrammatic view (side view: FIG. 6a, frontal view: FIG. 6b) where the viewer uses the embodiment of FIG. 5;

DETAILED DESCRIPTION

Figure 1:
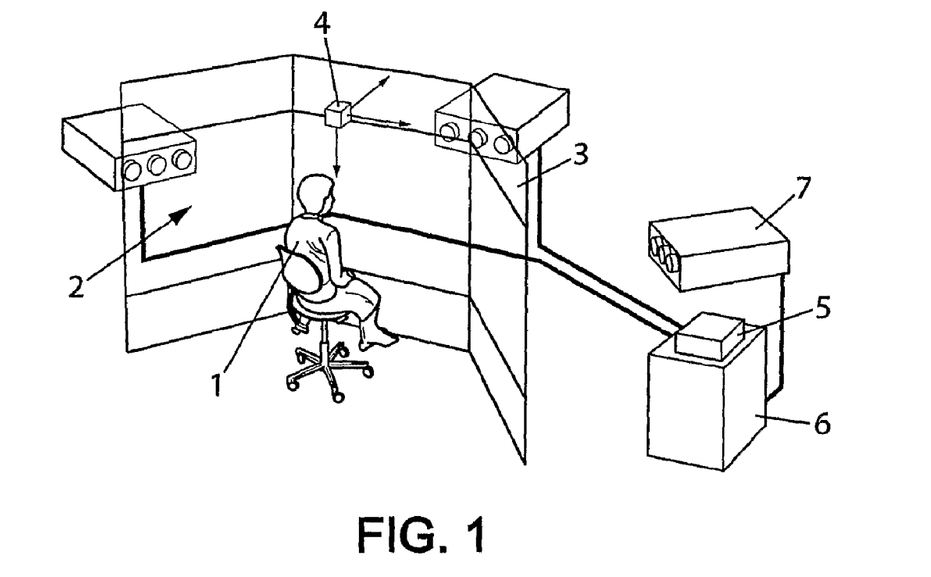
FIG. 1 shows a diagrammatic perspective view of a system according to the invention to implement the process of the invention where a stereoscopic scene is projected to the viewer.
Figure 2A:
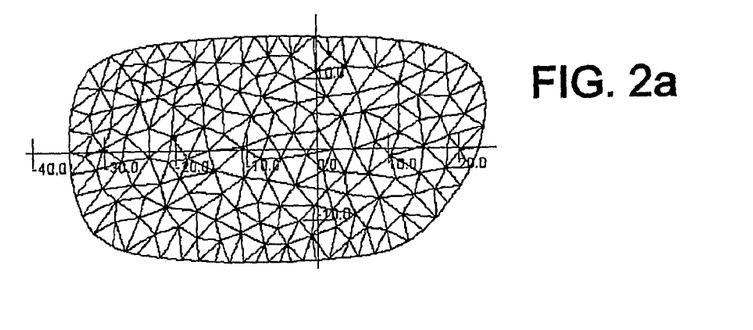
FIG. 2a diagrammatically shows initial meshing used to calculate the stereoscopic scene of FIG. 1.
Figure 2B:
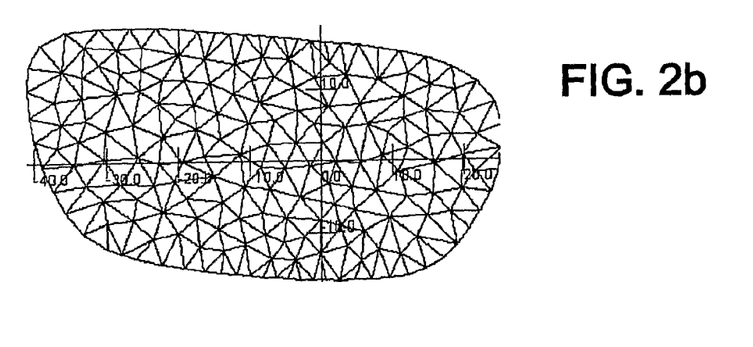
FIG. 2b diagrammatically shows calculated distortions at each intersection of the initial meshing.
Figure 2C:
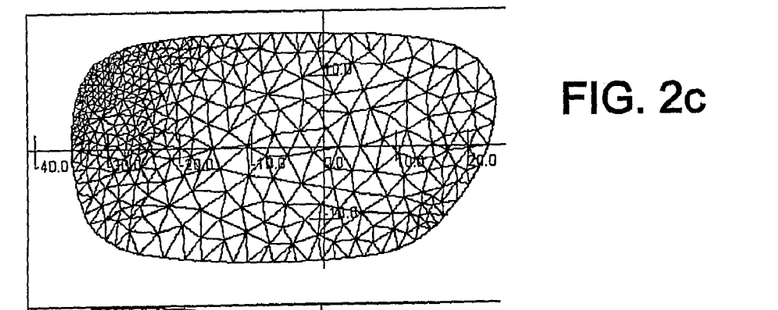
FIG. 2c diagrammatically shows an adapted meshing based on the calculated distortions.
Figure 2D:
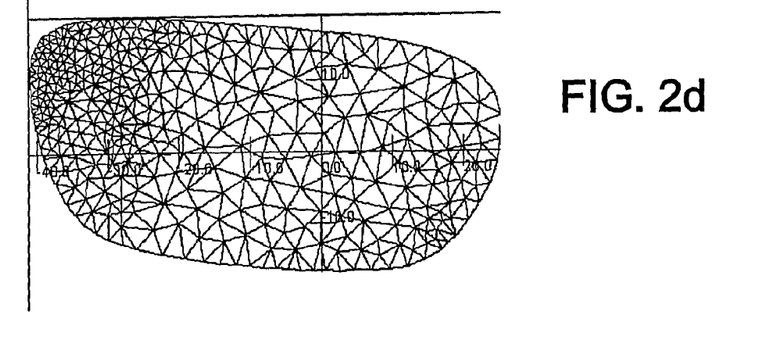
FIG. 2d diagrammatically shows recalculated distortions for the adapted meshing.
Figure 3:
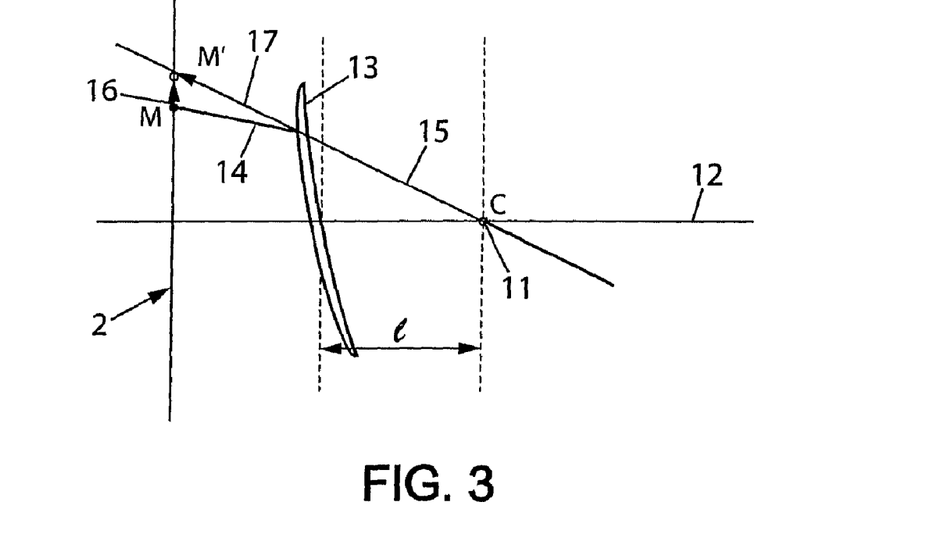
FIG. 3 shows a diagrammatic view of the optical path used to calculate the stereoscopic scene of FIG. 1.

FIGS. 1 to 3 relate to implementing a process according to the invention where a stereoscopic scene is projected to the viewer 1 and includes optical effect of a lens design, and where said scene 2 is calculated as a function of the viewer's head position.

The viewer 1 faces a three screens 3 stereoscopic display with 120° field of view. The position of the viewer's head is determined through a sensor 4 linked to a position calculator 5.

Said position calculator 5 is linked to computer 6 to input the viewer's head position. Computer 6 calculates a scene to be projected by 3 projectors 7 on screens 3.

Viewer 1 wears electro-active shutter glasses or polarized lenses to have a stereoscopic vision.

As for an example, sensor 4 is positioned on the head of the viewer, and is a position sensor for implementing virtual imaging, such as Fastrak Sensor commercialized by the company POLHEMUS. Other sensors such as Liberty commercialized by the company POLHEMUS, IS 900 commercialized by the company InterSence, or optical sensor such as ARTTrack commercialized by the company Advanced Real-time Tracking are also suitable.

As for an example, computer 6 uses a graphic card such as PNY Quadro® Fx 3000 G or Fx 4500 G.

The meshing used to calculate the optical effects, as a function of a given lens design and a given head's position, is shown on FIG. 2. The initial meshing of the zone through the right eyeglass is shown on FIG. 2a. Distortions corresponding to the vision through an eyeglass of a given lens design are calculated at each intersection of the meshing as shown on FIG. 2b. As a function of this calculation, a meshing adapted to the level of distortion is calculated, as shown on FIG. 2c and the distortions are recalculated with said meshing, as shown on FIG. 2d. It is then possible to obtain a precise perception of a scene as viewed with eyeglass lens of a given design.

A method to calculate optical effects is shown on FIG. 3 using ray tracing. Centre of rotation of the eye is referred as 11, viewing axis as 12, lens as 13, l is the distance between the optical centre of the lens and the centre of rotation of the eye 11. Incident ray 14, coming from a point M of the scene 2, is deviated by refraction through lens 13 to form a ray 15 converging to centre of rotation, C, of the eye 11, letting the viewer having the feeling that ray comes from a point M' as ray 17.

To take into account the lens design, corresponding distortion is introduced as a vector MM' 16 and initial point M is shifted to point M'.

Following an embodiment, computer 6 makes a calculation at each intersection point of meshing 2a or 2c to obtain the distortion level of 2b or 2d respectively, using said ray tracing, where the distortion corresponding to a lens design is stored in a database of computer 6.

FIGS. 4 to 7 relates to implementing a process according to the invention where the stereoscopic scene is an actual scene observed by the viewer through a device comprising an electro-active or an opto-active component suitable to reproduce the optical effect of a given lens design.

Figure 4A:
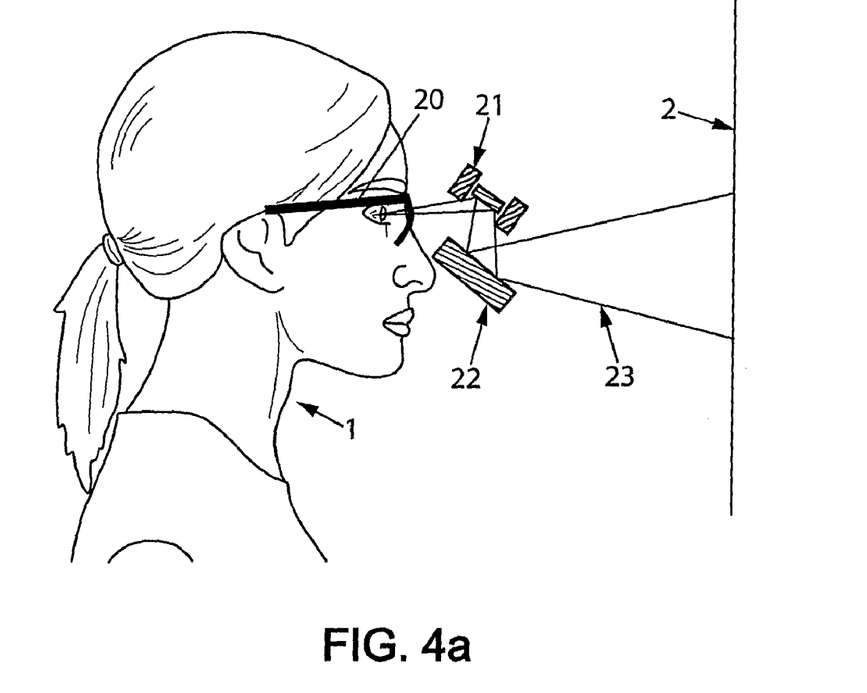
Figure 4B:
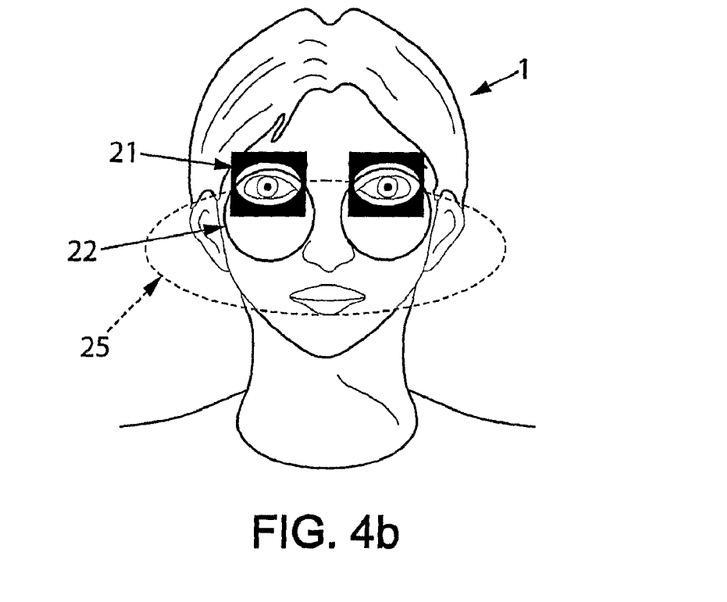
Figure 5:
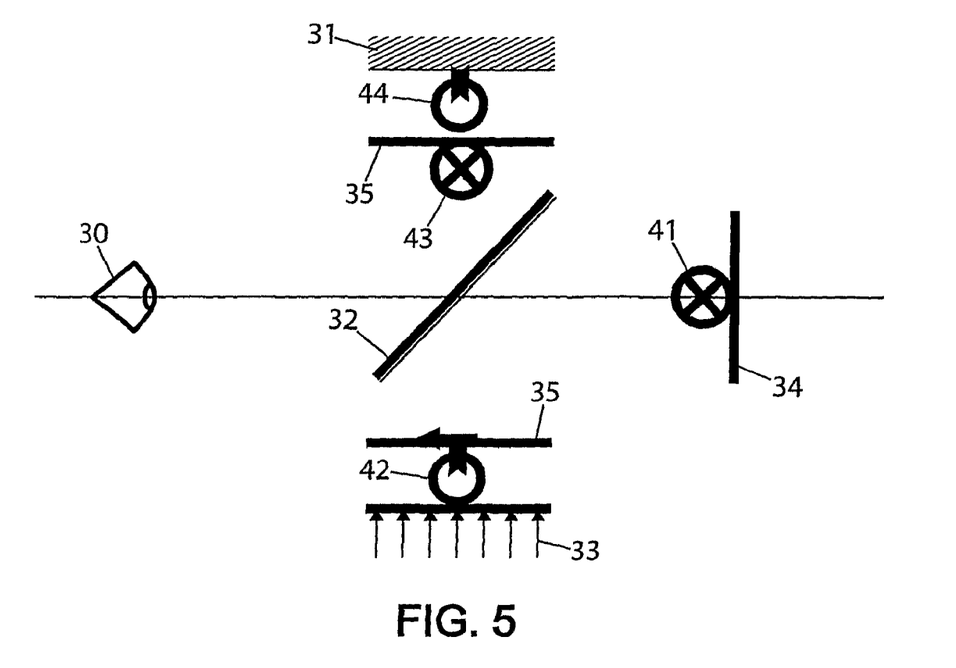
FIG. 5 shows a diagrammatic longitudinal section of another embodiment to implement the process of the invention where a device including an electro-active component is used.
Figure 6A:
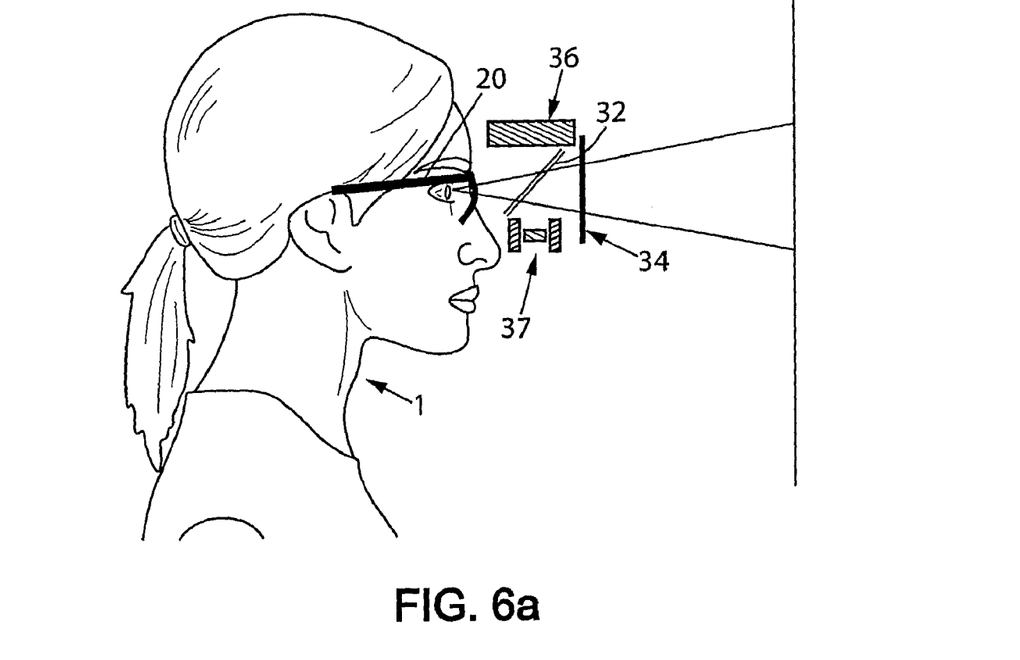
Figure 6B:
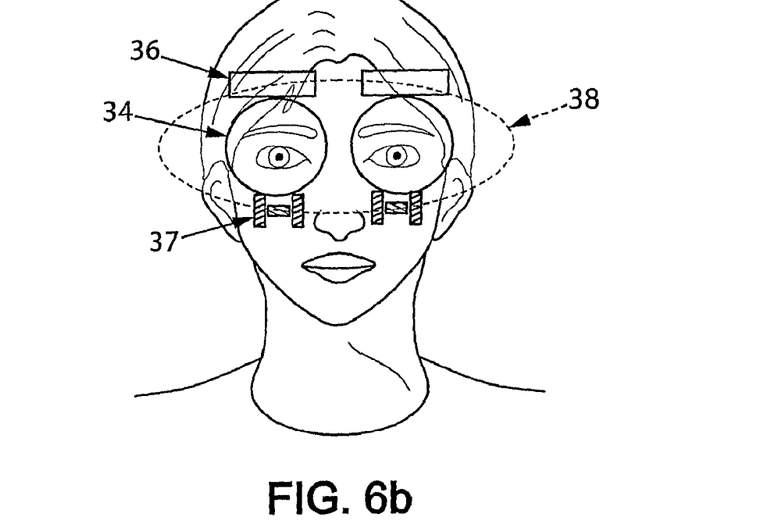

The electro-active component of the embodiments of FIGS. 4 to 6 is a deformable mirror.

In the system of FIG. 4, incident beam 23 coming from the scene 2 is firstly reflected on a plane mirror 22 to deformable mirror 21 and directed to the centre of rotation of the eye of the viewer 1. The vision field is delimited with a broken line 25, and is situated under the standard frontal vision field.

In the system of FIGS. 5 and 6, the vision field 38 is standard and frontal. Incident beam coming from the scene passes firstly through a polarizer 34, is entirely reflected on a two-ways mirror 32 to deformable mirror 33 after passing through quarter-wave plate 35. The reflected beam passes then again quarter-wave plate 35, through the two-ways mirror 32 and is entirely transmitted, through another quarter-wave plate 35 and is reflected on plane mirror 31. It is then entirely reflected on the two-ways mirror 32 and directed to the center of rotation of the eye 30 of viewer 1. The polarization of the light is indicated in the successive steps as 41, 42, 43, 44. Following this embodiment the viewer can see only the light which has been reflected on the deformable mirror 33.

Deformable mirror 33 and quarter-wave plate 35 are shown as a unique component 36 on FIGS. 6a and 6b, where plane mirror 31 and quarter-wave mirror 33 are shown as a unique component 37.

As shown on FIGS. 4 and 6, the viewer may wear lenses, such as spectacle lenses 20, in order to correct his far vision anomalies.

Following an embodiment the viewer wears PAL and the electro-active component modifies the viewed scene so that the viewer can see it as wearing different PAL designs.

Figure 7:
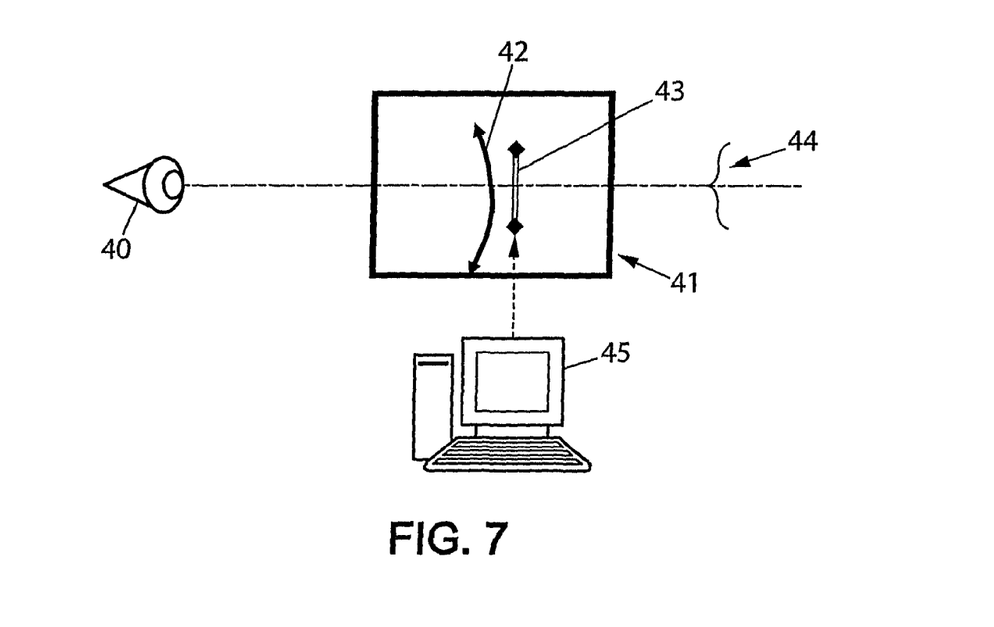
FIG. 7 shows a diagrammatic view of still another system according to the invention to implement the process of the invention where a device including an electro-active component is used.

In the system of FIG. 7, the electro-active component is a Spatial Light Modulator (SLM) 43 linked to a computer 45. Scene 44 is shown to eye 40 of the viewer through optical system 41 comprising said SLM 43 and far vision correcting or PAL lenses 42. Said SLM 43 can be addressed electrically, and is for example an Electrical Addressed Liquid Crystal SLM.

Figure 8:
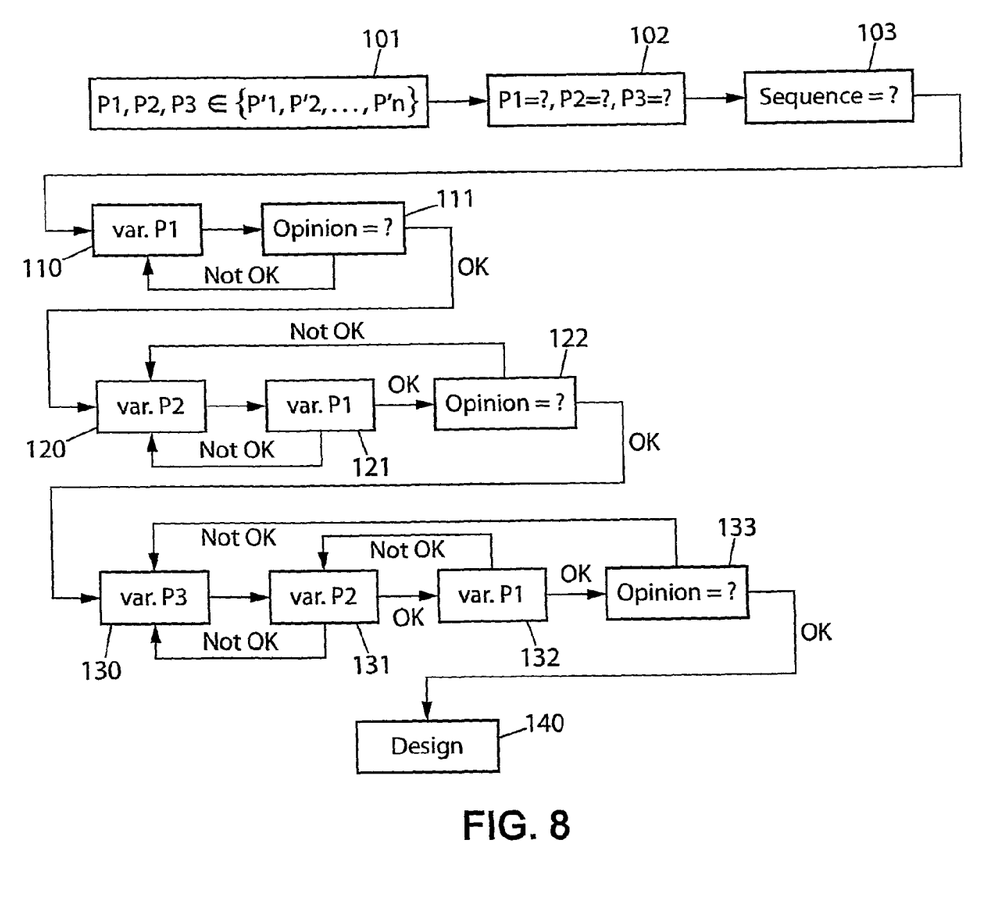
FIG. 8 shows a diagrammatic flow chart to implement a process according to the invention.

FIG. 8 shows a diagrammatic flow chart to implement a process according to the invention, where different steps of the customization process have been exemplified.

First step, 101, corresponds to the choice of a number of vision parameters, for example P1 to P2, to be selected in a list of possible vision parameters P'1 to P'N. For example, said parameters are curvature of the design lens to be tested, progression length of a PAL, near vision inset of a PAL, distance between near and far vision zones, channel length, eye/head coefficient or other vision parameter known by the man skilled in the art of vision correction.

Step two, 102, corresponds to the initialization of the process where the initial ranges of selected parameters P1 to P3 are entered.

Step three, 103, corresponds to the test sequence consisting of choosing the order of test of parameters P1 to P3.

A first test sequence 110 to 111 is performed where the viewer can test the lens design corresponding to the parameters which have been selected previously. The viewer expresses his opinion at step 111 and a new set of parameter P1 is selected and tested if the viewer is not satisfied and this step is repeated until the viewer's satisfaction.

A second test sequence 120 to 122 is performed where the viewer can test the lens design corresponding to the parameters P2, P3 which have been selected initially and with parameter P1 as previously selected. After varying parameter P2, a verification of the compatibility of previously selected parameter P1 in respect to selected parameter P2 is done. The test sequence 120 to 122 is repeated until the viewer's satisfaction relating to combined parameters P1 and P3, with selected parameter P2.

A third test sequence 130 to 133 is performed where the viewer can test the lens design corresponding to initially selected parameter P3 and previously selected parameters P2 and P1.

After varying parameter P3, a verification of the compatibility of previously selected parameter P2, then with previously selected parameter P1 is done. The test sequence 130 to 133 is repeated until the complete viewer's satisfaction and the design of an optimized design is obtained as far as parameters P1 to P3 are concerned. It is then possible to characterize the optimal eye-glass lenses for said particular viewer and to transmit corresponding manufacturing data to a manufacturing unit.

The invention is not restricted to the above described embodiments which can be varied in a number of ways within the scope of the claims.

The invention claimed is:

1. A method for determining an optimal eyeglass lens design for a viewer, where a design of a lens imparts optical correction of the lens, the method comprising the successive steps of:
   showing the viewer a stereoscopic scene including optical effects of a first lens design;
   introducing a relative movement between the viewer and the shown stereoscopic scene, said scene being shown with optical effects of the first lens design, so as to take into account how things are seen while wearing a lens with the first lens design;
   obtaining the viewer's opinion of the first lens design;
   showing the viewer a stereoscopic scene including optical effects of a modified lens design;
   introducing a relative movement between the viewer and the shown stereoscopic scene, said scene being shown with the modified lens optical effects so as to take into account how things are seen while wearing a lens with the modified lens design;
   obtaining the viewer's opinion of the modified lens design;
   repeating the three last steps up to viewer's satisfaction.

2. The method of claim 1 where the viewer's head position is determined and where the stereoscopic scene is a stereoscopic projected image calculated as a result of the lens design and the viewer's head position.

3. The method of claim 2 where the viewer's head position determination and the projection of calculated stereoscopic scene are dynamic.

4. The method of claim 3 where the stereoscopic scene is calculated by means of an operating unit comprising an optical effect data base and the optical effect data base is used to approximate the dynamically projected stereoscopic scene.

5. The method of claim 4 where the approximation to calculate the stereoscopic scene is based on distortion estimation calculated in a given plan independently of the actual distance of the object of the scene, using for example ray tracing.

6. The method of claim 2 where the stereoscopic scene is calculated by means of an operating unit comprising a lens design data base.

7. The method of claim 2 where the stereoscopic scene is calculated by means of an operating unit comprising an optical effect data base.

8. The method of claim 1 where the stereoscopic scene is an actual scene observed by the viewer through a device comprising an electro-active or opto-active component suitable to reproduce the optical effect of a given lens design.

9. The method of claim 8 where the electro-active or opto-active component is a liquid crystal spatial light modulator, which can be addressed electrically or optically respectively.

10. The method of claim 9 where the spatial light modulator is an electrically addressed liquid crystal SLM and is mounted so that an incident beam of light from the stereoscopic scene can be transmitted therethrough.

11. The method of claim 8 where the electro-active component is a deformable mirror.

12. The method of claim 11 where an incident beam of light from the stereoscopic scene is firstly reflected on a plane mirror and directed to the deformable mirror on which it is reflected and directed to the viewer's eyes.

13. The method of claim 11 where an incident beam of light from the stereoscopic scene is firstly polarised, then reflected on a semi-reflective mirror and directed to the deformable mirror, then directed through the semi-reflective mirror to a plan mirror and then directed to the viewer's eyes after being reflected on the semi-reflective mirror.

14. The method of claim 11 where the deformable mirror is a piezoelectric deformable mirror.

15. The method of claim 1 where the first lens design is determined using standard vision correction measurement of the viewer.

16. The method of claim 1 where a number of vision parameters are selected and test sequences are performed parameter by parameter, the viewer's opinion being obtained during each sequence corresponding to each parameter.

17. The method according to claim 16 where the influence of a vision parameter choice is tested on previous determined vision parameters, and if the result is unsatisfactory, a new test sequence is performed with previous determined vision parameters up to viewer's satisfaction.

18. The method according to claim 16, where vision parameters are chosen from the list constituted of: progression length, near vision inset, eye/head coefficient, curvature of the lens.

19. The method of claim 1 comprising further the step of transmitting data corresponding to optimal lenses design to a manufacturing unit.

20. The method of claim 19 where the manufacturing unit is a lens printer, such as an ultraviolet engraving system or a direct machining tool.

21. A computer program for carrying out the method of claim 1, the computer program dynamically calculating a stereoscopic scene based on input parameters comprising:
  viewer's head position parameters
  viewer's satisfaction parameters
  lens design data base that includes the surface characteristics and corresponding dioptric power of several model lens designs,
  wherein the computer program is configured to: receive the measured head position parameters and data of a lens design from a lens design data base, calculate the optical effects of the lens design data, which is the optical distortion due to said lens design; and dynamically calculate a stereoscopic scene corresponding to the head position parameters and the optical effects due to said lens design.

22. A computer program for carrying out the method of claim 1, the computer program actuating an electro-active component based on input parameters comprising:
  viewer's satisfaction opinion,
  lens design data base that includes the surface characteristics and corresponding dioptric power of several model lens designs,
  wherein the computer program is configured to: receive the measured head position parameters and data of a lens design from a lens design data base, calculate the optical effects of the lens design data, which is the optical distortion due to said lens design; and dynamically calculate a stereoscopic scene corresponding to the head position parameters and the optical effects due to said lens design.

* * * * *